United States Patent [19]

Utterberg

[11] Patent Number: 5,520,640
[45] Date of Patent: May 28, 1996

[54] BLOOD AIR TRAP CHAMBER

[76] Inventor: David S. Utterberg, 1080 Chestnut St., San Francisco, Calif. 94109

[21] Appl. No.: 254,428

[22] Filed: Jun. 6, 1994

Related U.S. Application Data

[63] Continuation of Ser. No. 876,039, Apr. 30, 1992, abandoned.
[51] Int. Cl.$^6$ .................................................. A61M 1/00
[52] U.S. Cl. ............................................................ 604/80
[58] Field of Search ........................... 604/80–85, 408, 604/409, 410, 414, 415, 416, 903; 128/DIG. 13

[56] References Cited

U.S. PATENT DOCUMENTS

| | | | |
|---|---|---|---|
| 2,210,098 | 8/1940 | Ravenscroft | 604/80 |
| 2,594,639 | 4/1952 | Gossett | 604/80 |
| 2,758,597 | 8/1956 | Elder | 604/80 |
| 4,217,328 | 8/1980 | Cambio, Jr. . | |
| 4,250,879 | 2/1981 | Muetterties | 604/81 |
| 4,334,535 | 6/1982 | Wilson et al. | 604/82 |
| 4,428,743 | 1/1984 | Heck | 604/4 |
| 4,512,764 | 4/1985 | Wunsch | 604/80 |
| 4,573,967 | 11/1986 | Hargrove et al. | 604/85 |
| 4,666,598 | 5/1987 | Heath et al. . | |
| 4,681,606 | 7/1987 | Swan, Jr. et al. . | |
| 4,882,575 | 11/1989 | Kawahara | 128/DIG. 13 |
| 4,998,914 | 3/1991 | Wiest et al. | 128/DIG. 13 |
| 5,061,365 | 10/1991 | Utterberg . | |
| 5,078,699 | 1/1992 | Hoben et al. | 604/80 |

FOREIGN PATENT DOCUMENTS

| | | |
|---|---|---|
| 0058325A1 | 1/1982 | European Pat. Off. . |
| 0134436 | 3/1985 | European Pat. Off. . |
| 0423841A1 | 4/1991 | European Pat. Off. . |
| 2845365 | 10/1978 | Germany . |

OTHER PUBLICATIONS

Printed Sheet entitled Drake–Willock 7000 or 7200.
Partial European Search Report—Appln. No. EP 93 30 3164.

*Primary Examiner*—C. Fred Rosenbaum
*Assistant Examiner*—Manuel Mendez
*Attorney, Agent, or Firm*—Gerstman, Ellis & McMillin, Ltd.

[57] ABSTRACT

A blood chamber for hemodialysis sets which comprises a sealed, flattened plastic parison, typically from blow molding, which defines a reservoir chamber and at least a first conduit communicating with a first end of the reservoir chamber through a first port. The conduit extends laterally along substantially the length of the reservoir chamber in spaced relation thereto, for connection with hemodialysis set tubing adjacent the reservoir chamber and opposed to the first end. The blood chamber typically also defines a second port communicating with the reservoir chamber, typically at the same end thereof as the first port.

45 Claims, 5 Drawing Sheets

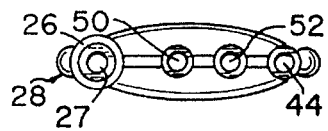
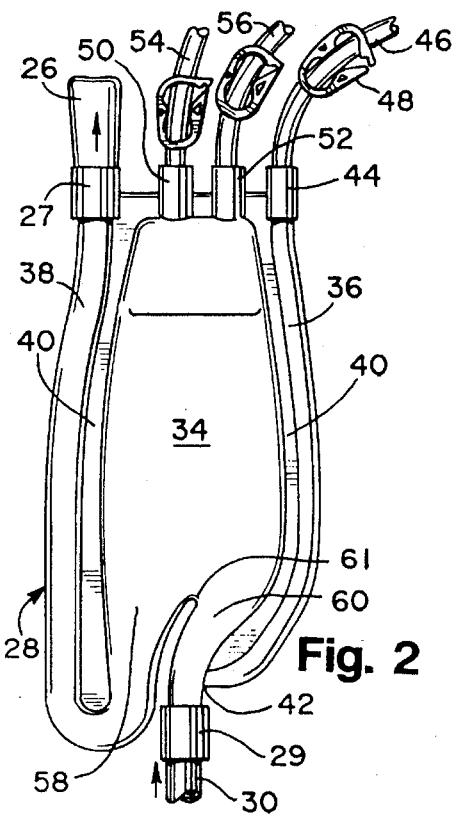
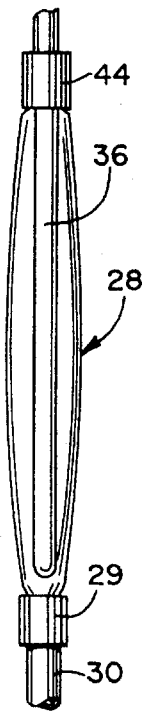
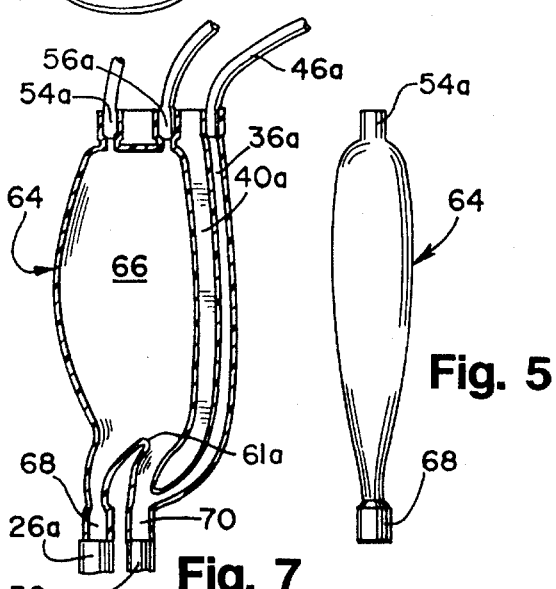
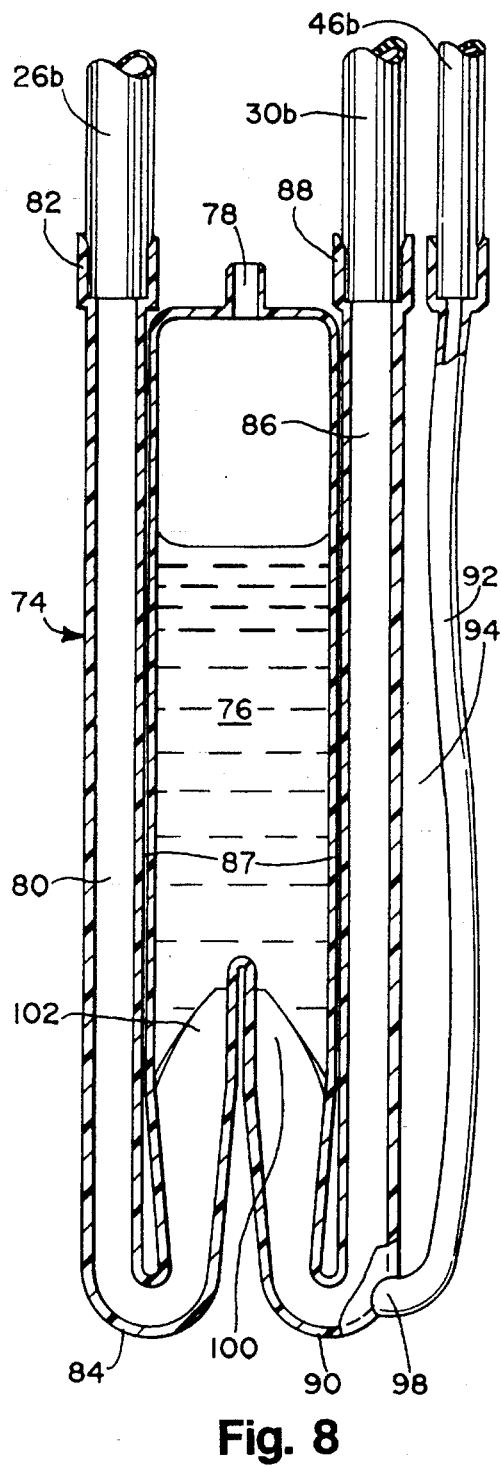

Fig. 11
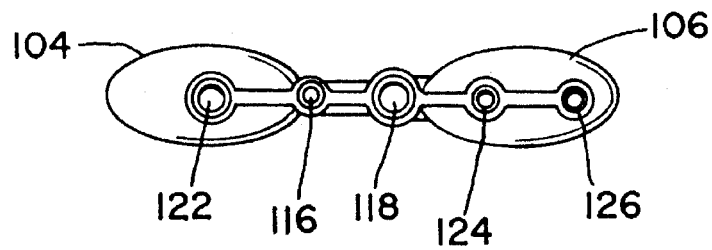
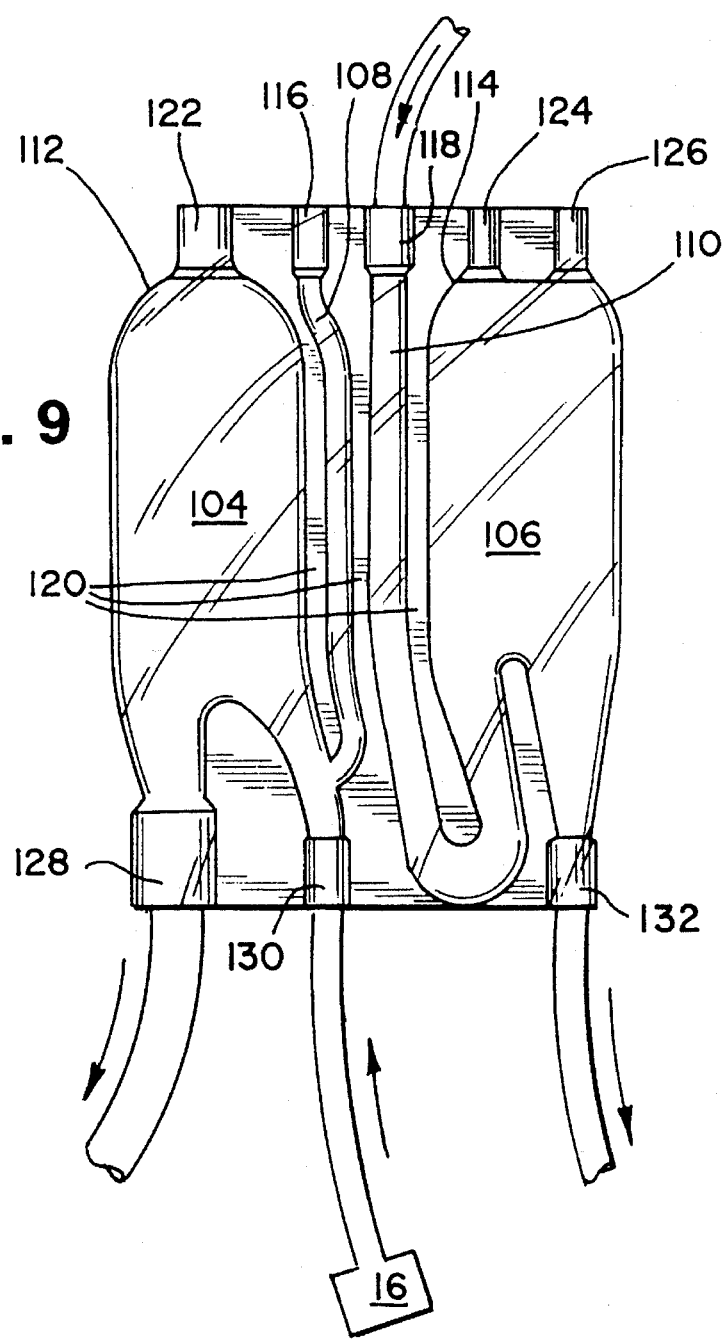
Fig. 9
Fig. 10

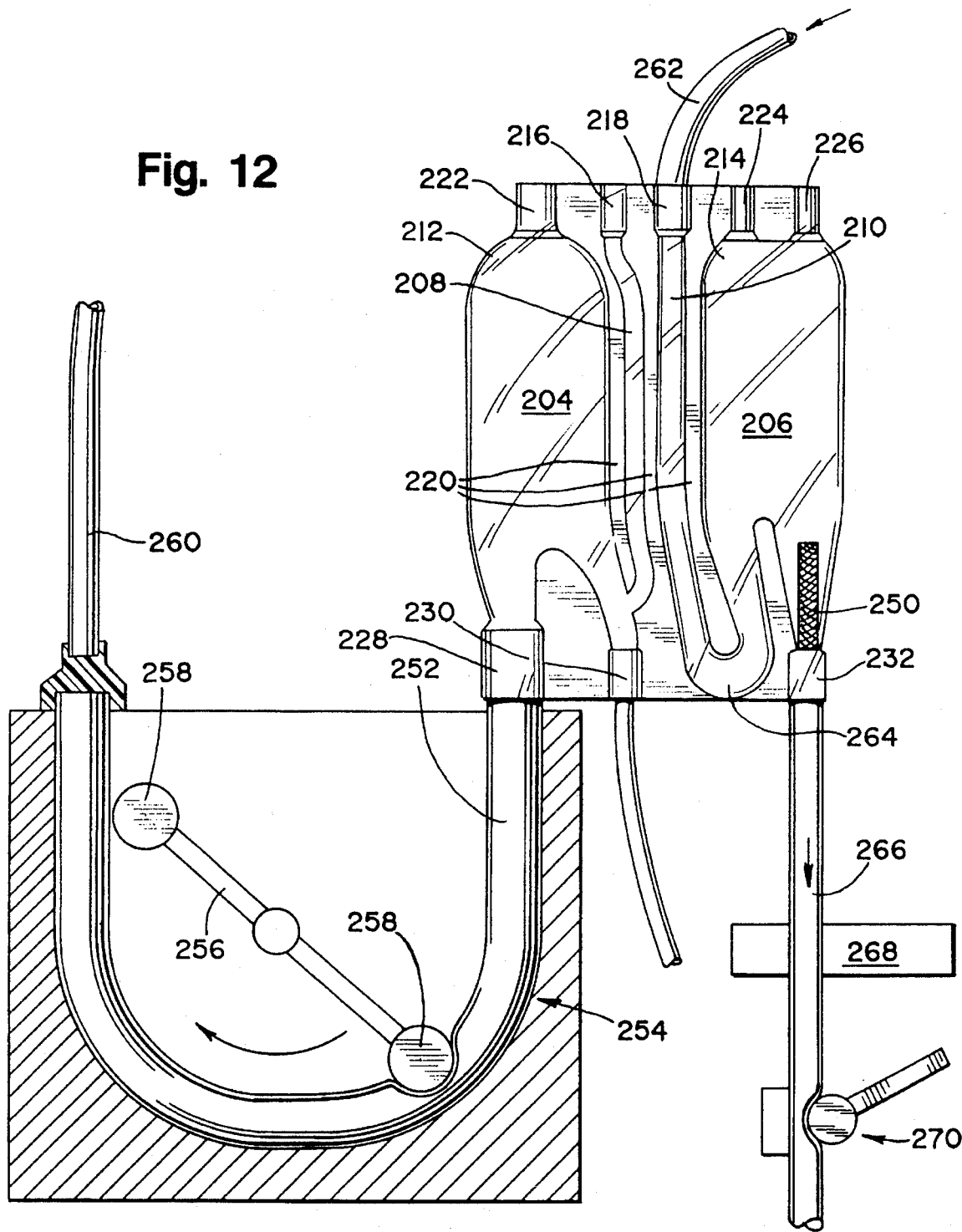

BLOOD AIR TRAP CHAMBER

This is a continuation of U.S. application Ser. No. 07/876,039, filed Apr. 30, 1992, now abandoned.

BACKGROUND OF THE INVENTION

At the present time, hemodialysis or plasmapheresis blood chambers, so called air-trap blood chambers or "drip chambers" are typically made from two injection molded parts, comprising a round top cap which is solvent bonded to cylindrical chamber. Flow typically proceeds from a blood tube access port in the top cap out through an exit port at the bottom of the chamber. This structure has the following problems:

1. The two part assembly of top cap to cylindrical chamber is expensive and prone to leak, and the residual solvent adhesive is potentially toxic to the blood.

2. These top caps and chambers are generally round in cross section for injection molding and assembly reasons. Otherwise leaks will occur even more frequently. However, the round shape leaves barely sufficient room for the three to four ports which must communicate through the top cap to the interior of the drip chamber. These access ports must fit typically within a 15–18 mm. O.D. (outer diameter) area of the top cap, eliminating the chance of directly connecting a pump segment to a drip chamber, which typically is a 12 mm. O.D. tube placed in a port having an O.D. of about 14 mm. Arterial drip chambers are always in close proximity to a pump segment but, because of the above, the drip chamber must be connected to the pump segment via a pump segment connector attached to a length of blood tube, the end of which can fit on the top cap. This is an expensive solution, also prone to leaks and high residuals of solvents.

3. Drip chambers are placed in arterial bloodlines either downstream of the pump segment ("post-pump") or upstream ("pre-pump"), depending on the prescription of the physician and the type of dialysis machine. Pre-pump arterial chamber bloodlines are more expensive to make because the IV saline port must often be mounted on a separate "T" connector upstream from the drip chamber. On "post-pump" bloodlines the IV saline port can be mounted on the inlet pump segment connector, thus saving one part and one tube and the assembly thereof. This combination connection also reduces leaks and solvent residuals.

There are a number of reasons why the IV saline port location is different in "pre-pump" and "post-pump" bloodlines, but each relates to the necessity of administering saline upstream from the arterial drip chamber:

a. During the priming procedure prior to dialysis, the arterial tubing upstream from the IV saline port must be retrograde primed. A drip chamber in this segment is difficult to retrograde prime.

b. During dialysis, saline infusion (for relief of hypotension) is most safely done if any entrained bubbles are caught by a downstream arterial drip chamber. Also, the saline flow can only be visualized if there is a drip chamber downstream.

c. During rinse-back of blood to the patient at the end of dialysis, the arterial fistula and the arterial blood tube upstream from the IV saline port must be retrograde flushed with saline to return this blood to the patient. To counteract the resistance of blood pressure, the saline bag is typically squeezed to create retrograde saline flow. This resistance is much greater if a drip chamber is upstream from the IV saline port. (Note: rinse-back of the downstream portion of the arterial and venous lines is done by the blood pump so resistance in this direction is unimportant). Further, retrograde rinse of blood tubing is desirably of "plug flow" type, resulting in little saline being added to the patient. If a drip chamber is upstream from the IV saline port, the blood in the drip chamber is diluted slowly by saline, resulting in large amounts of saline being administered to the patient. This is a problem, since one of the goals of dialysis is to remove fluid from the patient.

One partial solution to the problems of arterial chamber has been the use of blow-molding to make one piece chambers. Thus, the two part assembly problems discussed above are eliminated. The other problems remain.

Also, the blowmolded chambers in the literature are all so-called "bottom entry" chambers whereby the blood inlet port is at the bottom of the chamber and blood enters into the blood space at the bottom or sidewall of the chamber. (This is opposite to "top entry" chambers, all injection molded so far, where blood enters at or adjacent the top into the airspace above the blood.) Two problems of the bottom entry chambers as disclosed in Swan U.S. Pat. No. 4,681,606, Heath U.S. Pat. No. 4,668,598 and European Patent Application No. 0058325A1 are:

The inlet port enters the blood space at a point higher than the outlet port, and There is a diversion means to prevent inlet flow from breaking the surface of the blood space and causing foaming, such diversion directing the flow in the direction of the blood outlet.

The first problem is that blood must often be "rinsed-back" to the patient (at the end of dialysis) in a retrograde direction from the dialysis flow. With the inlet higher than the outlet, some blood will be caught in the chamber that cannot be returned to the chamber (the amount determined by the volume contained between the inlet and outlet).

The second problem is that any entrained air in the inlet blood stream is directed toward the outlet, which under certain circumstances or today's higher blood flows can escape. As the primary function of the chamber is as an air trap, this is a significant problem.

DESCRIPTION OF THE INVENTION

It is an object of this invention to create a one-piece, plastic, blow molded arterial or arterial-venous blood chamber, eliminating the problems of two-piece construction. It is another object of this invention to use typically blow molding to create an outboard blood inlet port preferably capable of being connected directly to a pump segment tube, thus eliminating the above-discussed problems of additional parts and tubes. It is a third object of this invention (independent of the second object) to use blow molding to provide an IV saline port integral with the blood inlet of the chamber, thus eliminating the problems of a separate IV saline "T" connector construction as discussed above. As another independent object, a plastic blood chamber may be provided in which the blood flow can be run in either direction, for greater usefulness.

It is a fifth object to make an inlet diverter that directs blood flow and entrained air away from the blood outlet, plus a chamber with equal height inlet and outlet for reversible flow efficiency.

The chamber may be used in a pre-pump mode. In other embodiments, this same chamber can be connected in a post-pump mode, thereby reversing the flow direction and changing the pre-pump mode integral IV saline port into an integral heparin port.

The blood pump operates in the same direction for both manufactured blood lines in the pre-pump mode and the post-pump mode. In the pre-pump mode the blood air trap chamber of this invention is under subatmospheric or negative pressure because the blood chamber is between the blood pump and the arterial fistula needle, which latter needle is the point of major flow resistance. In the post-pump mode the chamber of this invention is under superatmospheric or positive pressure since the chamber is between the pump and the venous fistula needle, which is another major point of flow resistance.

Physicians are sometimes worried about stressing a patient's fistula. Thus they like to use pre-pump designs because the negative pressure in the pre-pump tubing segments can be monitored, giving the doctor an idea of how much the patient's fistula is in danger of collapse.

In other situations, doctors worry more that the dialyzer will clot up, so they prefer to use post-pump designs because the positive pressure in the post-pump tubing segments can be monitored, giving the doctor an indication that the resistance in the dialyzer is increasing.

The blood chamber of this invention may be used particularly for hemodialysis sets. The chamber comprises a sealed, round or flattened plastic tube which defines a reservoir chamber and at least one conduit communicating with a first end of the reservoir chamber through a first port, for connection with blood flow tubing of a hemodialysis set. A conduit extends laterally along substantially the length of the reservoir chamber in spaced relation thereto, for connection with another blood flow tubing of a hemodialysis set adjacent the reservoir chamber end which is opposed to the first end.

The blood chamber also defines a second port communicating with the reservoir chamber at the same end thereof as the first port. This second port may also connect with blood flow tubing of the set, so that in the pre-pump mode the blood flow can pass from the second port, through the blood chamber, and to and through the first port as it passes through the set.

The flattened plastic tube described above also preferably defines a second conduit extending laterally along the reservoir chamber in spaced relation to it. The second conduit communicates with the reservoir chamber through one of the blood inlet and blood outlet ports. Typically, the second conduit may be for the administration of saline solution, or the like, in the pre-pump mode or heparin in the post pump mode or the like. The blood chamber of this invention may preferably define at least four or more separate conduits which are communicating directly with the reservoir chamber.

It is preferred for the one conduit described above to connect directly with roller pump tubing for blood flow, with this connection being positioned adjacent the opposed reservoir chamber end. The one conduit may be of any desired transverse dimension adjacent the opposed reservoir chamber to accommodate the connection with the roller pump tubing in a manner that does not crowd out the desired or necessary other ports and apertures into the blood chamber.

It is also preferred, in accordance with this invention, for the first and second ports of the reservoir chamber to terminate inwardly at substantially identical longitudinal positions in the blood chamber. In other words, they occupy an "equal height" in the blood chamber, contrary from the current configuration in an arterial chamber for a dialysis set, where the blood inlet to the blood chamber is usually higher than the outlet. By the arrangement of this invention, it becomes practical to run the blood reversely through the arterial chamber, when and as that is desired, with effective operation and flow of blood therethrough, and without loss of a significant amount of blood within the arterial chamber. Thus, more blood can be returned to the patient in the back flush step of dialysis with reverse flow through the arterial chamber of this invention.

In one preferred embodiment especially in the pre-pump mode the inlet is positioned to divert blood flow away from the outlet.

In another preferred embodiment, the second port of the blood chamber communicates with a second conduit extending laterally along substantially the length of the reservoir chamber in spaced relation thereto. Preferably, the reservoir chamber, the one conduit, and the second conduit are all defined by a single, integral plastic parison, being formed typically by a known blow molding process.

Also, it may be preferred for the integral parison to also define a third conduit which communicates with the second port, and which extends laterally along substantially the length of the reservoir chamber. The second and third conduits may be used respectively for blood flow and for the addition of saline, heparin, or other desired materials to the system.

The chamber may define a plurality of first access ports adjacent to a first chamber end, one of which is a blood pump segment access port (inlet or outlet) capable of mating with a blood pump tube of typically 9.0 to 14 mm. OD. This blood pump segment port can lead into the main cavity of the chamber at its bottom, side or top. Another first access port or ports may be for pressure measurement, sample withdrawal or medication administration.

A second blood access port may be provided at a second, opposed end of the chamber, and is typically capable of mating with a plastic blood tube of typically 5.0 to 8.5 mm. OD. This second blood access port can also lead into the body of the chamber at the bottom, side or top. Flow in this chamber may be from blood tube to pump segment or vice versa (i.e. pre-pump or post-pump). In one embodiment, the chamber defines a plurality of first access ports adjacent to a first chamber end, none of which are blood pump segment or blood tubing ports. This is, they are only ports for pressure measurement, sample withdrawal or medication administration. At a second, opposed end of the chamber a plurality of ports are defined, one of which is a blood pump segment access port capable of mating with a plastic tube of typically 9.0 to 14 mm. O.D. The other access port is capable of mating with a plastic blood tube of typically 5.0 to 8.5 mm. O.D. Both blood access ports can enter the main cavity of the chamber at the bottom, side or top.

In another embodiment, the chamber defines a plurality of first access ports adjacent to a first chamber end, two of which are blood access ports for blood tubing and a blood pump segment. At a second, opposed end of the chamber there are no ports.

An additional access port may extend from either the first end or the second end, but it preferably enters into the cavity of the chamber just above the blood tube port. This serves for the administration of IV saline in a "pre-pump" drip chamber or for administration of heparin or anticoagulant in a "post-pump" drip chamber.

The plastic arterial chambers of this invention may then be assembled into an arterial set for hemodialysis, or may be co-blow molded with a venous chamber to form a "cassette" that may be assembled into an arterial/venous set for hemodialysis.

A fluid flow chamber cassette is described by Heath et al. U.S. Pat. No. 4,666,598. The following is an improvement on that invention.

In another aspect of our invention, a blowmolded chamber cassette results in fewer leaks, smoother blood pathways and lower manufacturing cost than the injection molded, front-to-back assembly of the Heath device.

Yet another aspect is the chamber design wherein all tubing ports are substantially in-line with the long axis of the cassette chambers. Heath describes a cassette wherein transverse tubing ports must be employed, giving expense of construction as well as rough handling of the blood as it transits from axial direction to transverse direction.

Another aspect following on axial tubing port construction is a unique blood pump orientation. Traditional peristaltic blood pumps are in the form of an upside-down U. This relates to the design of currently available blood chambers. Heath describes a bloodpump in the form of a backwards C, offering some benefits, but at the expense of complicated production method. We describe a blood pump in the form of an U, which has many benefits:

a. Unlike Heath, only one end of the pump segment need be tethered to the cassette, again reducing cost of construction. The pump segment is formed straight, and is curved by the curve of the stator of the pump housing. Heath, on the other hand, is curved into a backwards C by the presence on the cassette of two transverse mounted pump segment connectors. This complicates the molding and assembly methods required.

b. Unlike upside-down U pumps, the described U pump segment primes easily. Pump segments able to provide high bloodflow rates have large inner diameters, in the range of 8 mm or more. In order not to crush delicate blood cells, peristaltic pump rollers are calibrated to leave a small gap between the pump segment walls when being crushed by the rollers. This gap, however, leaks air quite readily making it difficult for enough vacuum to be created to lift the initial column of saline up to prime the pump segment. With a U pump segment, gravity causes the saline to fall into the pump segment, thereby priming it.

c. A U blood pump easily allows bottom-entry, bottom exit arterial chamber, which is well known to handle rapid bloodflows with less turbulence and foaming than top-entry chambers.

DESCRIPTION OF THE DRAWINGS

Referring to the drawings,

FIG. 2 is an elevational view of the blood chamber of this invention as used in FIG. 1a, but in reversed position;

FIG. 3 is an elevational view of the blood chamber of FIG. 2 rotated 90° about its longitudinal axis;

FIG. 4 is a top plan view of the blood chamber of FIG. 2;

FIG. 5 is an elevational view of another embodiment of blood chamber of this invention;

FIG. 6 is a top plan view of the blood chamber of FIG. 5;

FIG. 7 is an elevational view of the blood chamber of FIG. 5, rotated 90° about the longitudinal axis thereof;

FIG. 8 is an elevational view of another design of blood chamber in accordance with this invention;

FIG. 9 is an elevational view of a double blood chamber, made from a single flattened, plastic tube, to provide, for example, both the arterial and the venous blood chambers for a dialysis procedure in a single unit;

FIG. 10 is an elevational view of the blood chamber assembly of FIG. 9, rotated 90° about the longitudinal axis thereof;

FIG. 11 is a top plan view of the blood chamber of FIG. 9.

FIG. 12 is a partially schematic, fragmentary view of a dialysis set up showing a blowmolded, multiple chamber cassette similar to that shown in FIGS. 9–11 mounted on a dialysis machine; and FIG. 13 is a top view of the cassette of FIG. 12.

DESCRIPTION OF SPECIFIC EMBODIMENTS

Figure 1A:
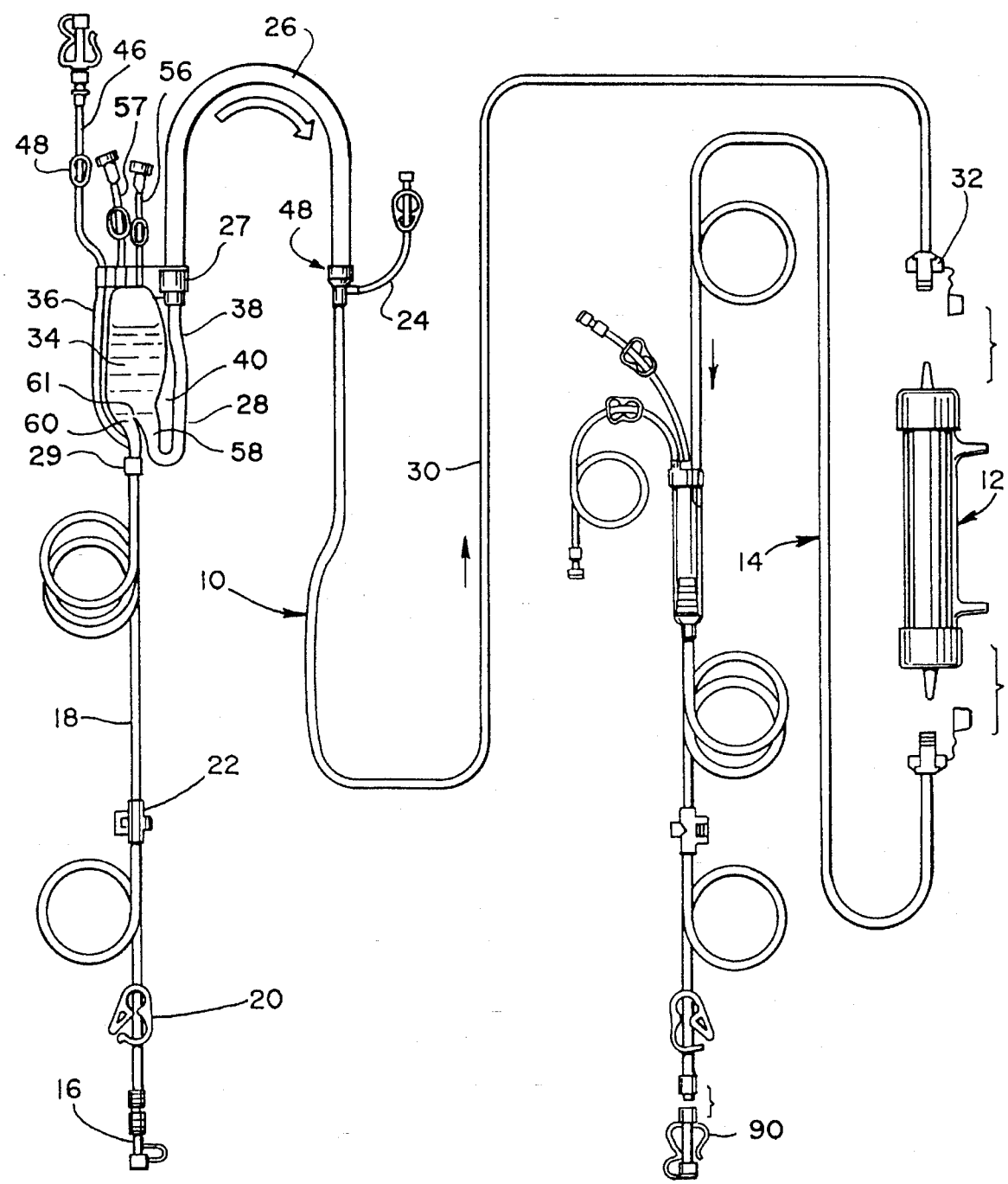
FIGS. 1a and 1b are plan views of an arterial set using the blood chamber of this invention, respectively in the pre-pump and post-pump modes, ready for connection with a conventional dialyzer and venous set.

Referring to FIG. 1a, an arterial pre-pump set 10 for hemodialysis is shown, along with a conventional hollow fiber dialyzer 12 and a conventional venous set 14, with the various parts being shown ready for assembly with each other in conventional manner. Apart from the novel disclosures herein, arterial set 10 is also shown of conventional design.

A luer lock patient arterial fistula needle connector 16 is provided on one end of set 10 as shown, with the set tubing 18 extending through an on-off clamp 20, and injection site 22, extending to connect with inlet port 29 of blood chamber 28 of this invention.

Roller pump segment 26 is shown to directly connect with blood outlet port 27 of blood chamber 28, and extends to a pump segment connector 48, and then to tube 30 extending to connector 32 for dialyzer 12. A heparin line 24 also connects to connector 48.

Venous set 14 has similar components as shown, which are of conventional design and thus do not need to be recited.

Figure 1B:
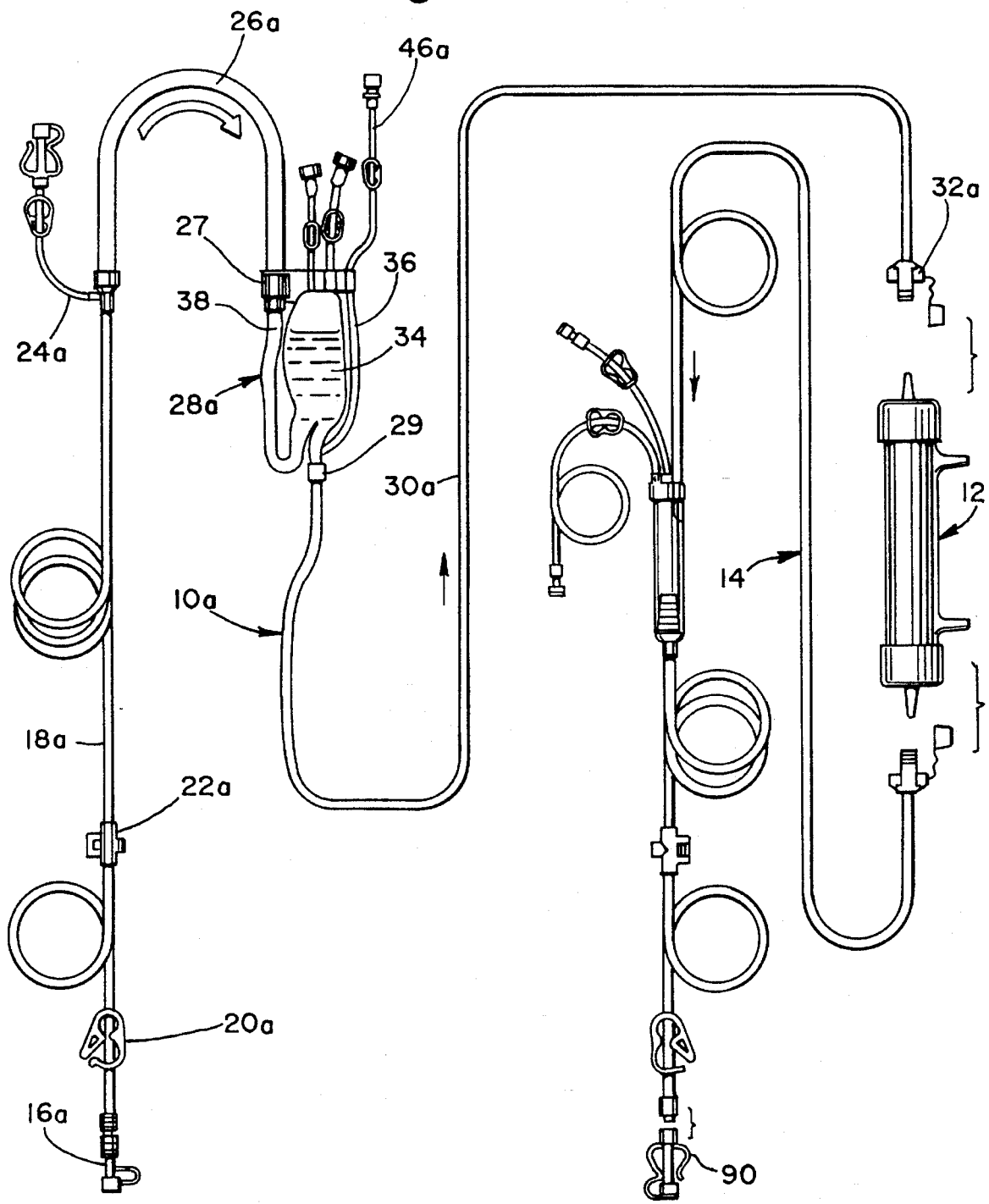

Referring to FIG. 1b, a similar arterial post-pump set 10a is shown, being of very similar design to the pre-pump set 10 except as otherwise described. A luer lock patient arterial fistula needle connector 16a, as before, is provided at one end of set 10a, with set tubing 18a extending through on-off clamp 20a and injection site 22a, in a manner similar to the previous set. However, in this embodiment, tubing 18a connects directly with pump tubing 26a. Heparin line 24 connects at the junction between tubings 18a, 26a, on the other end of pump tubing 26a because of the different pressure considerations in the post-pump mode. Heparin must always be administered against a positive pressure rather than a reduced pressure, to avoid the catastrophic occurrence of the heparin syringe discharging its entire contents in a few seconds into the patient in the event of heparin pump failure.

Pump tubing 26a communicates with blood chamber 28a at blood port 27 of the chamber. It can be seen that chamber 28a may be the very same chamber as chamber 28, being merely reversed and with different connections. This provides a significant convenience in manufacturing and inventory control since the same chamber of this invention may be used in both situations without any change of design. Then, set tubing 30a communicates directly with port 29 of blood chamber 28a, terminating in a connector 32a as in the previous embodiment.

This setup may then communicate with a dialyzer 12 and a venous set 14 as in the previous embodiment.

Referring also to FIGS. 2–4, blood chamber 28 or 28a may be made, typically, through a blow molding process of a moderately stiff thermoplastic, as is known in the prior art so that there may be formed out of a single, plastic, tubular parison the following: a reservoir chamber 34, and a pair of conduits 36, 38 extending laterally along reservoir chamber 34, being spaced from the chamber by flat-sealed portions 40 of the plastic parison. Conduit 38 directly communicates with pump segment tube 26 through port 27, with adequate room for such connection being available since the various ports 27, 44, 50, 52 are distributed in a transverse line. Conduit 38 then extends the entire length of reservoir chamber 34 to communicate therewith at the opposite end of chamber 34.

Conduit 36 connects in branch-connection relation 42 with blood port 29. Conduit 36 also extends the length of reservoir chamber 34, spaced therefrom by one of the flat seals 40 to a connector 44, for connection with a IV saline access tube in the pre-pump mode 46 having a conventional squeeze clamp 48. In the post-pump mode the tube 46a serves as a heparin tube.

Furthermore, at the end of blood chamber 28 which is remote from blood port 29, additional ports 50, 52 can be provided for respective connection with a pressure monitor line 54 and an air adjust or medication tube 56.

Reservoir chamber 34 is capable of flat-collapse under a predetermined suction pressure in the manner of prior art blood chambers for the known, desirable purposes.

Normally, blood is pumped by a roller pump from arterial patient connector 16 or 16a into reservoir chamber 34. From there, the blood flows out of the reservoir chamber, to pass through the remainder of the dialysis setup as shown in FIG. 1.

By this invention the first and second ports have inner ends 58, 60 separated by partition 61 which occupy substantially identical longitudinal positions along the blood chamber as particularly shown in FIG. 2, contrary to the prior art, where generally reservoir chambers have inlet ports that terminate deeper or higher within the reservoir chamber than the outlet port. It can be seen that in the pre-pump mode of FIG. 1a inner end 60 serves as the inlet to the reservoir, and that the inlet is constructed to cause the inlet stream of blood to be directed laterally away from the outlet 58 by means of a curvature in partition 61. The effect of this is to keep entrained air in the blood away from the outlet until the air bubbles have had a chance to rise to the top of the blood level and join an air bubble 63 typically found there.

Also because of this modification, it becomes possible to effectively and completely run blood in reverse through the system, by reversal of the roller pump that operates on pump tubing 26, so that blood can be returned to the patient through the arterial side as saline is added to the system, for example through tube 46 or 46a. Thus, at least some of the blood can flow back to the patient through connector 16 or 16a in a manner that is called "plug flow" by which it is meant that the blood does not mix to a large degree with the saline solution which is being used to replace it, so that the patient receives little more fluid than that which is found in his own blood, as the blood is returned to him or her from the dialysis set at the end of dialysis. This provides significant advantage to the dialysis procedure and the effective return of a maximum amount of blood to the patient after the dialysis procedure with a minimum of saline solution.

Referring to FIGS. 5 through 7, another embodiment of blood chamber for a dialysis set is disclosed. Blood chamber 64 may be made by blow molding as before, from a single, tubular parison to define a reservoir chamber 66 having a pair of bottom ports 68, 70. Bottom port 68 may directly communicate with pump tubing 26a in a manner similar to the communication with pump tubing 26 in the previous embodiment, pre-pump mode, to provide blood flow out of chamber 66. Inlet flow of blood passes through port 70 and blood conduit 30a in a manner analogous to the prior embodiment. This chamber may also be used in post-pump mode.

At the opposite end of blood chamber 64, a port 54a may be provided for the pressure monitor, while another port 56a may be provided for air adjustment or the administration of medication.

An integral access tube 36a is also provided, being formed from the original, blow molded parison and integral with reservoir chamber 66 through a spaced, flattened, solid portion 40a of the original parison. Conduit 36a communicates at one end with an IV or saline tube 46a as in the previous embodiment, in pre-pump mode, extending laterally along the length of reservoir chamber 66 to join with port tube 70 so as to be in communication with reservoir chamber 66. In post-pump mode, conduit 36a connects to a heparin line.

As before, an arterial hemodialysis set having a blood chamber of such a design is capable of backflushing of blood in chamber 66 and upstream therefrom back into the artery of the patient in a flow pattern which is reverse from the normal flow pattern, with good "plug flow" and the other advantages of such an arrangement. Also partition 61a is curved to facilitate bubble separation as described above.

Since the end of blood chamber 64 that carries ports 68, 70 has only two ports, it is possible to use a port 68 which has adequate size to directly receive pump segment 26a, for the advantageous elimination of an intermediate part and to reduce the number of solvent-sealed connections.

Referring to FIG. 8, another embodiment of this invention is shown, comprising a blood chamber 74 which, as before, is made out of a single, tubular plastic parison by blow molding.

Blood chamber 76 is shown, having an upper end with a single port 78, which may be used for connection with a pressure monitor, for example. A first, connected conduit 80 is shown having a connection 82 with pump tubing 26b in a manner similar to the previous embodiments. First conduit 80 then extends the entire length of reservoir chamber 76, making a U-turn 84 at the other end thereof into an open aperture communicating with reservoir chamber 76.

A second, connected inlet conduit 86 is also provided on the other side of reservoir chamber 76, communicating at its upper end with blood tubing 30b in a manner similar to the previous embodiments through connector 88. Second, connected conduit 86 then extends the length of reservoir chamber 76, being integrally formed therewith through plastic web 87, down to another U-turn 90, which communicates with the interior of blood chamber 76 as does first connected conduit 80.

Thus, in the pre-pump mode blood is pumped through a set by means of a pump acting on pump tubing 26b, which is directly connected to second conduit 80. The blood passes through first conduit 86, and then enters reservoir chamber 76. The blood exits reservoir chamber 76 through second conduit 80, to travel on through the dialysis setup via blood tube 30b.

Additionally, a third connected tube 92 is formed out of the same parison by blow molding, to be integrally connected to the remainder of the blood chamber by plastic web 94, which like web 87, is a part of the parison. Connected tube 92 may be, in turn, connected to saline tubing 46b, with third conduit 92 extending the length of reservoir chamber 76, and joining with second, connected conduit 86 at a junction point 98, which is typically near curved portion 90. Thus, as before, blood can flow normally into reservoir chamber 76 through first connected conduit 80 and out of the chamber through second connected conduit 86.

Obvious modifications may be made for post-pump use. For reverse flow through reservoir chamber 76, in a manner similar to the embodiment of FIG. 2, the inlet ports 100, 102 of the respective conduits 86, 80 terminate inwardly as shown at substantially identical longitudinal positions in the blood chamber 76, to permit easy reverse flow through the chamber. This provides advantages as previously discussed.

Turning to FIGS. 9 through 11, in this embodiment, a single, blow-molded parison may form blood pre-pump arterial chamber 104 and venous chamber 106, for use in a combined arterial-venous hemodialysis set. Each of blood chambers 104, 106 defines a respective conduit 108, 110 which communicates with a first end 112, 114 of the reservoir chamber through a respective first port 116, 118.

In each case, the respective conduits 108, 110 are separated by flattened portions 120 of the parison from their respective chambers 104, 106 and each other, with the conduits extending laterally along substantially the length of each reservoir chamber 104, 106 in spaced relation thereto, in accordance with this invention.

Thus, a unitary, double chamber is provided for equipping a dialysis set with pre-pump and post-pump blood chambers, for example, or for any other desired use.

Port 116 may be used for saline infusion when chamber 104 is under negative pressure and for heparin infusion if it is under positive pressure as in the post-pump mode. Port 128 may be in connection to the pump tubing, while port 130 comprises the arterial blood inlet. Ports 122, 124 and 126 connect to pressure monitors or serve as medication application ports. Port 118 connects from the venous connector of the dialyzer, while port 132 connects to the venous patient connector. However, the multiple chamber cassette of this invention may be connected in other ways as desired.

Referring to FIGS. 12 and 13, the cassette shown is made of a single blowmolded parison to define a pair of chambers 204, 206, similar in virtually all respects to the cassette of FIGS. 9 through 11, and like reference numerals in the two hundreds corresponding to the same reference numerals in the one hundreds of the cassette of FIGS. 9 through 11.

It can be seen that all tubing ports are substantially parallel with the long axis of cassette chambers 204, 206. This provides an improvement of easier handling of the blood over, for example, transverse entry ports.

Connected to port 228 is pump tubing 252, which is shown to be mounted in a roller pump housing 254 so that pump tubing 252 is maintained in a U-shaped configuration which is right-side up rather than upside down or on its side, as shown. The track of housing 254 defines the shape of the pump tubing 252. The roller pump with its arms 256 and rollers 258 functions in the known and normal manner to pump blood so that blood enters the system in one specific mode from the patient artery through inlet port 230 into chamber 204, and out of chamber 204 through port 228 into pump tubing 252. Then, the blood is pumped through tubing 260 to a dialyzer.

The blood from the dialyzer then enters tubing 262 to pass through port 218 and separate conduit 210 to extend the length of venous chamber 206; to effect a U-turn 264, and to enter the venous chamber. Then, the blood passes through filter 250, through outlet port 232 and tubing 266 to pass back to the patient's venous system, while moving across ultra sonic air detector 268, and line clamp 270, both of conventional design.

By this embodiment, only one end of the pump segment 252 needs to be tethered to a cassette. This greatly reduces the cost of construction. The pump segment 252 may be formed straight, with the curvature being provided by the curve of the stator or track 254 of the pump housing.

Likewise, because the pump tubing 252 is formed in a right-side-up U segment, as described above, high blood flow rate tubing in the range of 8 mm. inner diameter or more may be readily primed, since the segment readily fills with liquid and stays filled.

Also, such a blood pump allows the use of bottom entry, bottom exit arterial chamber 204, which is well known to handle rapid blood flows with less turbulence and foaming than top entry chambers.

This invention may be used as desired with single, separate chambers of any design, or with single, blowmolded chambers, or with a multiple blowmolded cassette chamber as shown.

The above has been offered for illustrative purposes only and is not intended to limit the scope of the invention of this application, which is as defined in the claims below.

That which is claimed:

1. In a hemodialysis set which comprises blood tubing, roller pump tubing, and a blood chamber, said blood chamber comprising a reservoir chamber and at least a first conduit communicating with a first end of the reservoir chamber through a first port, said first conduit extending laterally along substantially the length of said reservoir chamber in laterally connected but spaced relation thereto, said blood chamber defining a second conduit extending along substantially the length of said reservoir chamber and communicating with the reservoir chamber at the same end thereof as said first port, said first conduit connecting directly with said roller pump tubing adjacent a reservoir end opposed to said first end, said first and second ports of the reservoir chamber terminating inwardly toward said reservoir chamber at substantially identical longitudinal positions in said blood chamber.

2. The hemodialysis set of claim 1 in which said first and second ports are separated by a central partition, said partition defining a lateral angle to cause inflow from one of said ports to be directed laterally away from the other of said ports, whereby air bubbles entering through the one of said ports are less likely to be immediately caught and sucked out of the chamber through the other of said ports.

3. The hemodialysis set of claim 2 in which said flattened plastic tube also defines a second conduit extending laterally along said reservoir chamber in spaced relation thereto, said second conduit communicating with said reservoir chamber through said second port.

4. The hemodialysis set of claim 3 in which said flattened plastic tube defines at least four separate ports communicating directly with said reservoir chamber.

5. The hemodialysis set of claim 1 in which said reservoir chamber, first conduit, and second conduit are defined by said flattened plastic tube.

6. The hemodialysis set of claim 5 in which said integral tube also defines a third conduit which communicates with said second port and which extends laterally along substantially the length of said reservoir chamber.

7. A hemodialysis set which defines hemodialysis blood tubing, roller pump tubing, and a blood chamber connected thereto, said blood chamber comprising a reservoir chamber and at least a first conduit communicating with a first end of the reservoir chamber through a first port, said conduit extending laterally along substantially the length of said reservoir chamber in laterally connected but spaced relation thereto, for connection with tubing adjacent the reservoir chamber end opposed to said first end, said blood chamber defining a second port communicating with the reservoir chamber at the same end thereof as the first port, said first conduit connecting directly with roller pump tubing for blood flow, adjacent said opposed reservoir chamber end.

8. The hemodialysis set of claim 7 which defines a second conduit extending laterally along said reservoir chamber in spaced relation thereto, said second conduit communicating with said reservoir chamber through one of said first and second ports.

9. The hemodialysis set of claim 8 in which said second port communicates with said second conduit extending laterally along substantially the length of the reservoir chamber in spaced relation thereto, said reservoir chamber, first conduit, and second conduit being defined by a collapsed and sealed plastic tube.

10. The hemodialysis set of claim 9 in which said integral parison also defines a third conduit which communicates with said second port and which extends laterally along substantially the length of said reservoir chamber.

11. The hemodialysis set of claim 10 in which said first and second ports of the reservoir chamber terminate inwardly at substantially identical longitudinal positions in said blood chamber.

12. The hemodialysis set of claim 11 in which said flattened, plastic tube defines at least four separate conduits communicating directly with said reservoir chamber.

13. The hemodialysis set of claim 9 in which said first and second ports are separated by a central partition, said partition defining a lateral angle to cause inflow from one of said ports to be directed laterally away from the other of said ports, whereby air bubbles entering through the one of said ports are less likely to be immediately caught and sucked out of the chamber through the other of said ports.

14. In hemodialysis apparatus, a hemodialysis set which defines arterial and venous blood chambers on opposed sides of a roller pump which defines flexible tubing and a roller to collapse said tubing, and tubing communicating with said pump tubing and arterial and venous sets with a dialyzer, the improvement comprising, in combination, one of said blood chambers directly communicating with said pump tubing through a first port, said pump tubing comprising collapsible flexible tubing formed into a configuration of an upright U-shape by mounting in a roller pump track, whereby said roller pump tubing is easily primed.

15. The hemodialysis system of claim 14 in which said chamber defines a blood inlet and blood outlet that connect with said blood chamber at a lower end of said blood chamber.

16. The hemodialysis system of claim 15 in which said blood chamber defines at least one conduit communicating with one of the blood inlet and blood outlet of said chamber, said conduit extending laterally along substantially the length of said blood chamber in spaced relation thereto, for connection with hemodialysis set tubing adjacent the blood chamber end opposed to said blood inlet and outlet end.

17. The hemodialysis system of claim 15 in which said blood inlet and blood outlet are separated by a central partition, said partition defining a lateral angle to cause inflow from said blood inlet to be directed laterally away from said blood outlet whereby air bubbles entering through said blood inlet are less likely to be immediately caught and sucked out of the chamber through said blood outlet.

18. A blood flow set which comprises a blood chamber for removing gas bubbles from blood, said blood chamber comprising a first port directly connected to a length of pump tubing without an intervening length of flexible tubing, and a second port also defined in said blood chamber, said blood flow set being mounted in hemodialysis apparatus with said pump tubing being installed in a roller pump assembly with said pump tubing being positioned in the shape of substantially a vertical U.

19. The set of claim 18 in which said blood chamber comprises a plastic tube which is collapsed and sealed together to define a reservoir chamber, and at least one conduit communicating with a first end of said reservoir chamber through a port thereof and extending laterally along substantially the length of the reservoir chamber in spaced relation thereto, said one conduit being directly connected with an end of said length of pump tubing.

20. The set of claim 19 in which the first port connected with said one conduit and said second port are both positioned to connect with said blood chamber at the lower end of said blood chamber.

21. The set of claim 20 in which said ports of the reservoir chamber terminate inwardly at substantially identical longitudinal positions in the blood chamber.

22. The blood flow set of claim 21 in which said first ports of the reservoir chamber are separated by a central partition, said partition defining a lateral angle to cause inflow from one of said ports to be directed laterally away from the other of said ports, whereby air bubbles entering through one of said ports are less likely to be immediately caught and sucked out of the chamber through the other of said ports.

23. The set of claim 20 in which said one conduit and the entry to the blood chamber from said first port are separated by a central partition, said partition defining a lateral angle to cause inflow from one of said ports to be directed laterally away from the other of said ports, whereby air bubbles entering through the one of said ports are less likely to be immediately caught and sucked out of the chamber through the other of said ports.

24. The blood chamber of claim 19 in which a second port communicates with a second conduit extending laterally along substantially the length of said reservoir chamber in spaced relation thereto, said reservoir chamber, one conduit, and second conduit being defined by said collapsed and sealed tube.

25. The blood chamber of claim 24 in which said collapsed and sealed tube also defines a third conduit which communicates with said second port and which extends laterally along substantially the length of said reservoir chamber.

26. The blood flow set system of claim 18 in which said pump tubing is positioned in the shape of substantially an upright U.

27. The blood flow set of claim 18 in which said blood chamber further comprises an intravenous solution conduit being positioned to run substantially the entire length of said blood chamber from one end to the other and to communicate with said chamber at a position adjacent the second port.

28. The blood flow set of claim 27 in which the connection of said one conduit and the pump tubing is at one end of the blood chamber, and said second port communicates with said blood chamber at the other end thereof.

29. The blood set of claim 18 in which the connection of said first port and the length of pump tubing is at one end of the blood chamber and the second port communicates with the blood chamber at the other end thereof.

30. A blood chamber for blood flow sets which comprises a plastic tube which is collapsed and sealed together to define a reservoir chamber and at least one conduit communicating with a first end of the reservoir chamber through a first port, said conduit extending along substantially the entire length of said reservoir chamber in laterally connected but spaced relation thereto, for connection with set tubing adjacent the reservoir chamber end opposed to said first end, said reservoir chamber and said one conduit being formed from said collapsed and sealed plastic tube, said blood chamber further defining a second port communicating with the reservoir chamber through said first end.

31. The blood chamber of claim 30 which is part of a hemodialysis set, said hemodialysis set having a blood inlet through said second port and a blood outlet through said first port.

32. The hemodialysis set of claim 31 in which said conduit defines an outer end positioned adjacent the end of said blood chamber opposed to said first and second ports, said outer conduit end being in direct communication with a length of U-shaped roller pump tubing.

33. The blood chamber of claim 30 in which a second conduit communicates with said first end of the reservoir chamber through said second port, said second conduit extending along substantially the entire length of said reservoir chamber in laterally connected but spaced relation thereto, for connection with blood flow set tubing adjacent the reservoir chamber end opposed to said first end.

34. The blood chamber of claim 33 in which said second conduit is positioned on a side of said reservoir chamber which is opposed to a side of said chamber adjacent to said one conduit.

35. The blood chamber of claim 34 in which said first and second ports terminate inwardly at substantially identical longitudinal positions to permit easy reverse flow through said chamber.

36. The blood chamber of claim 33 in which a third conduit communicates with said first end of the reservoir chamber, said third conduit extending along said reservoir chamber in laterally connected but spaced relation thereto, for connection with a source of intravenous solution at a position adjacent the reservoir chamber end opposed to said first end, whereby intravenous solution may be added to said chamber below the blood level of said chamber.

37. The blood chamber of claim 36 in which said third conduit communicates with the chamber through said first port, said first port being an inlet port.

38. The blood chamber of claim 33 in which said second conduit is positioned on a side of said reservoir chamber which is opposed to a side of said chamber adjacent to said one conduit, and further in which a third conduit communicates with said first end of the reservoir chamber, said third conduit extending along said reservoir chamber in laterally connected but spaced relation thereto for connection with a source of intravenous solution at a position adjacent the reservoir chamber end opposed to said first end, whereby intravenous solution may be added to said chamber below the blood level of said chamber.

39. The blood chamber of claim 38 in which said third conduit communicates with the chamber through said first port and said third conduit extends along substantially the entire length of said reservoir chamber, said first port being a blood inlet port.

40. The blood chamber of claim 39 in which said first and second ports terminate inwardly at substantially identical longitudinal positions, to permit easy reverse flow through said chamber.

41. The blood chamber of claim 30 in which another conduit communicates with said first end of the reservoir chamber, said other conduit extending along said reservoir chamber in laterally connected but spaced relation thereto, for connection with a source of intravenous solution at a position adjacent the reservoir chamber end opposed to said first end, whereby intravenous solution may be added to said chamber below the blood level of said chamber.

42. The blood chamber of claim 41 in which said other conduit communicates with the chamber through said first port, said first port being an inlet port, said other conduit extending along substantially the entire length of said reservoir chamber.

43. A blood chamber for hemodialysis sets, which comprises a plastic tube which is collapsed and sealed together to define a reservoir chamber; a conduit communicating with a first end of the reservoir chamber through a first port, said conduit extending laterally along substantially the length of said reservoir chamber in laterally connected but spaced relation thereto for connection with a source of intravenous solution at a position adjacent the reservoir chamber end opposed to said first end.

44. The blood chamber of claim 43 in which said conduit communicates with the chamber through a blood flow access port of said chamber, whereby intravenous solution may be added to said chamber below the blood level in the chamber.

45. The blood chamber of claim 43 in which a second conduit communicates with said first end of the reservoir chamber through said second port, said second conduit extending along substantially the entire length of said reservoir chamber in laterally connected but spaced relation thereto, for connection with a blood flow set adjacent the reservoir chamber end opposed to said first end.

* * * * *